(12) United States Patent
Farber

(10) Patent No.: US 7,585,402 B2
(45) Date of Patent: Sep. 8, 2009

(54) METHOD OF SENSOR CONDITIONING FOR IMPROVING SIGNAL OUTPUT STABILITY FOR MIXED GAS MEASUREMENTS

(75) Inventor: Boris Farber, Solon, OH (US)

(73) Assignee: BJR Sensors, LLC, Chargin Falls, OH (US)

(*) Notice: Subject to any disclaimer, the term of this patent is extended or adjusted under 35 U.S.C. 154(b) by 682 days.

(21) Appl. No.: 11/152,971

(22) Filed: Jun. 15, 2005

(65) Prior Publication Data

US 2005/0284772 A1      Dec. 29, 2005

Related U.S. Application Data

(60) Provisional application No. 60/580,606, filed on Jun. 18, 2004, provisional application No. 60/599,513, filed on Aug. 9, 2004.

(51) Int. Cl.
G01N 27/407 (2006.01)

(52) U.S. Cl. ............ 205/784.5; 205/781; 204/425

(58) Field of Classification Search ............ 205/775, 205/781, 784.5; 204/424, 425; 73/23.31, 73/23.32
See application file for complete search history.

(56) References Cited

U.S. PATENT DOCUMENTS

| | | | |
|---|---|---|---|
| 3,616,274 A | 10/1971 | Eddy | |
| 4,384,935 A * | 5/1983 | De Jong | 204/406 |
| 4,500,391 A * | 2/1985 | Schmidt et al. | 205/783 |
| 4,541,899 A | 9/1985 | Mase et al. | |
| 4,541,900 A | 9/1985 | Mase et al. | |
| 5,130,002 A | 7/1992 | Murase et al. | |
| 5,173,167 A | 12/1992 | Murase et al. | |
| 5,433,830 A | 7/1995 | Kawai et al. | |
| 5,780,710 A | 7/1998 | Murase et al. | |
| 5,980,728 A | 11/1999 | Farber et al. | |
| 6,200,443 B1 * | 3/2001 | Shen et al. | 204/401 |
| 6,401,522 B1 | 6/2002 | Kon et al. | |
| 2003/0047452 A1 * | 3/2003 | Jain et al. | 204/421 |

* cited by examiner

Primary Examiner—Kaj K Olsen
(74) Attorney, Agent, or Firm—John D. Gugliotta, PE, ESQ.

(57) ABSTRACT

A method of sensor conditioning is proposed for improving signal output stability and differentiation between responses to different gases such as exhaust from combustion processes. A square wave (or saw tooth) voltage pulses of opposite polarity and equivalent amplitude are applied between sensor electrodes. Pulses are separated by pauses, when charging power supply is disconnected from the sensor and sensor discharge is recorded. Useful information regarding concentration of analyzed gases can be extracted from two measurement methods.:
1. Measuring open circuit voltage decay during the pause immediately following voltage pulse.
2. Measuring the charging current during positive (negative) pulses and the discharging current during pauses following voltage pulses.

6 Claims, 20 Drawing Sheets

Sensor discharge with both electrodes exposed to air.

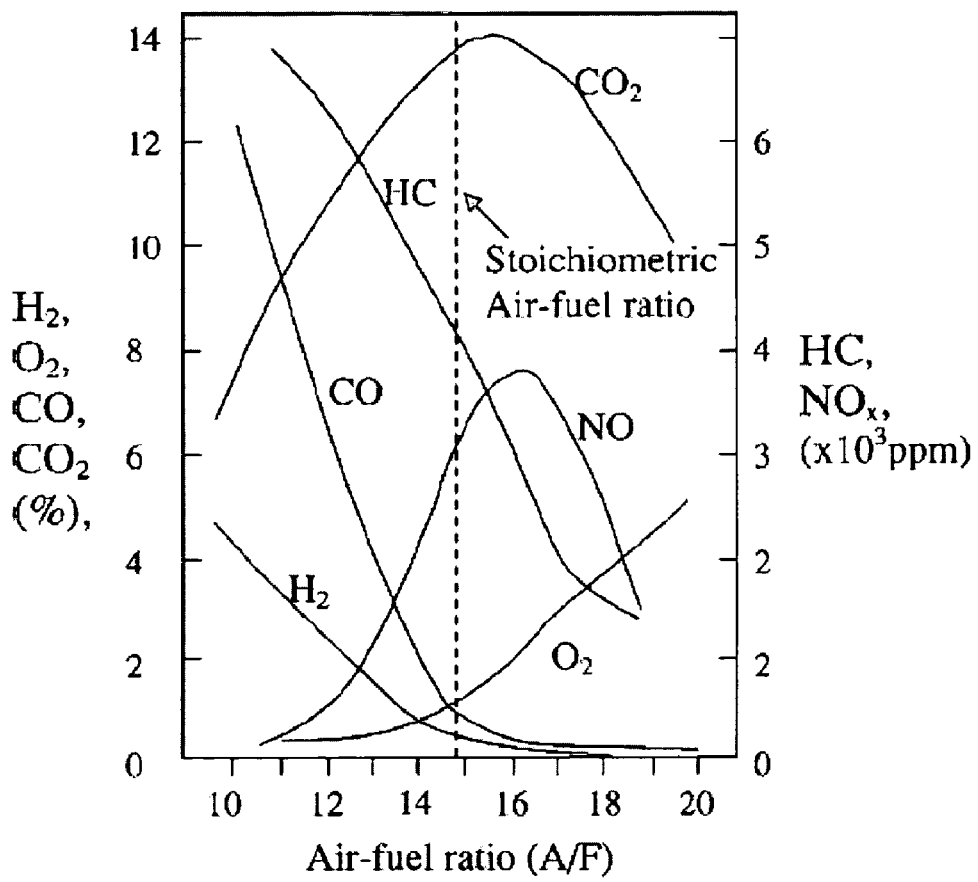
PRIOR ART
Figure 1. Schematic representation of combustion process exhaust (See J-H-Lee, "Review on Zirconia air-fuel ratio sensors for automotive applications" Journal of Materials Science, v. 38, pp 4247-4257, 2003)

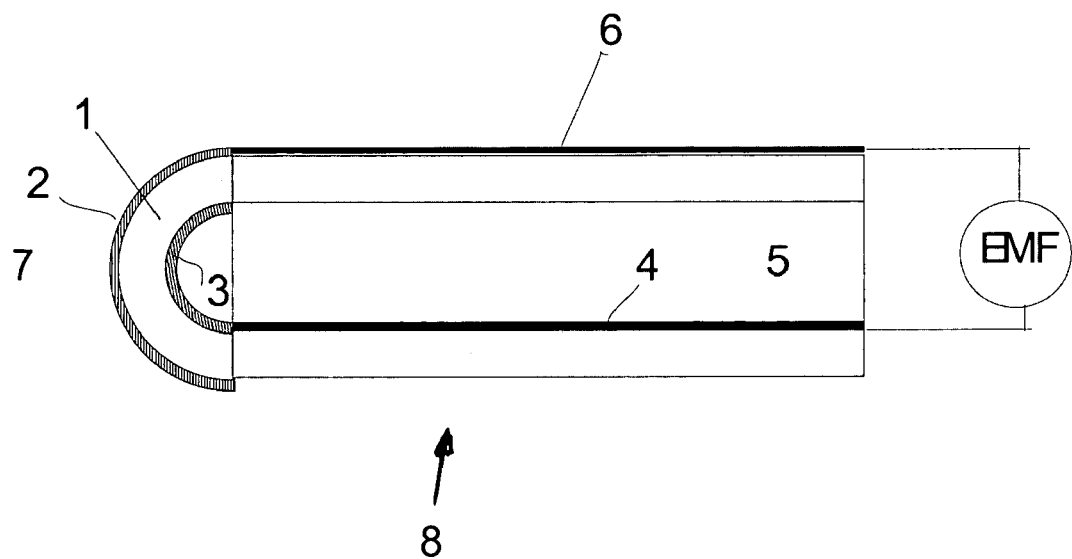
PRIOR ART
Figure 2. Schematic of Zirconia Oxygen sensor.
1- Zirconia substrate 2-Measuring electrode; 3 – Reference Electrode; 4&6 Connecting Leads; 5 Air; 7 Analyzed gas.

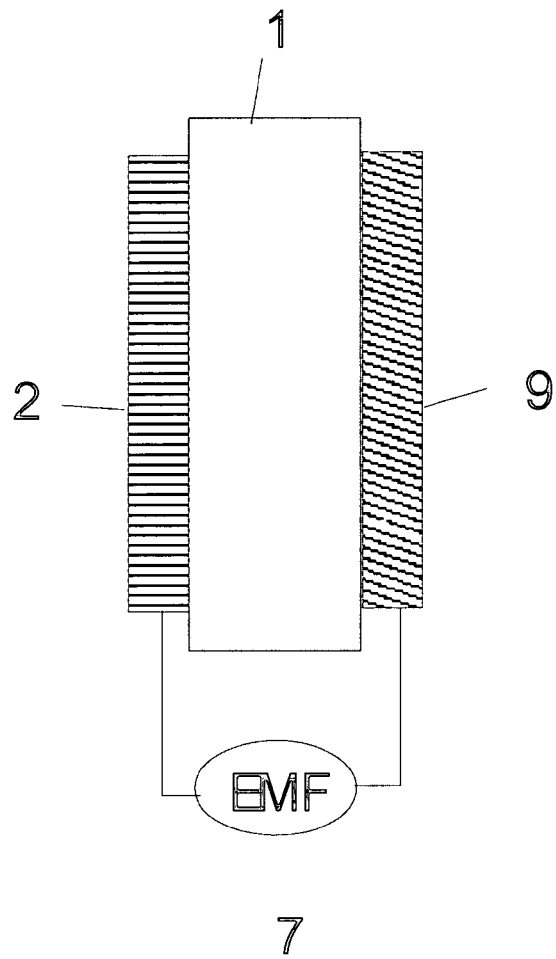
PRIOR ART
Figure 3. Schematic diagram of a mixed potential sensor with two electrodes exposed to analyzed gas (type 1).
1- Solid Electrolyte, 2-Measuring electrode, 9 – Second Measuring Electrode; 7 – Analyzed gas.

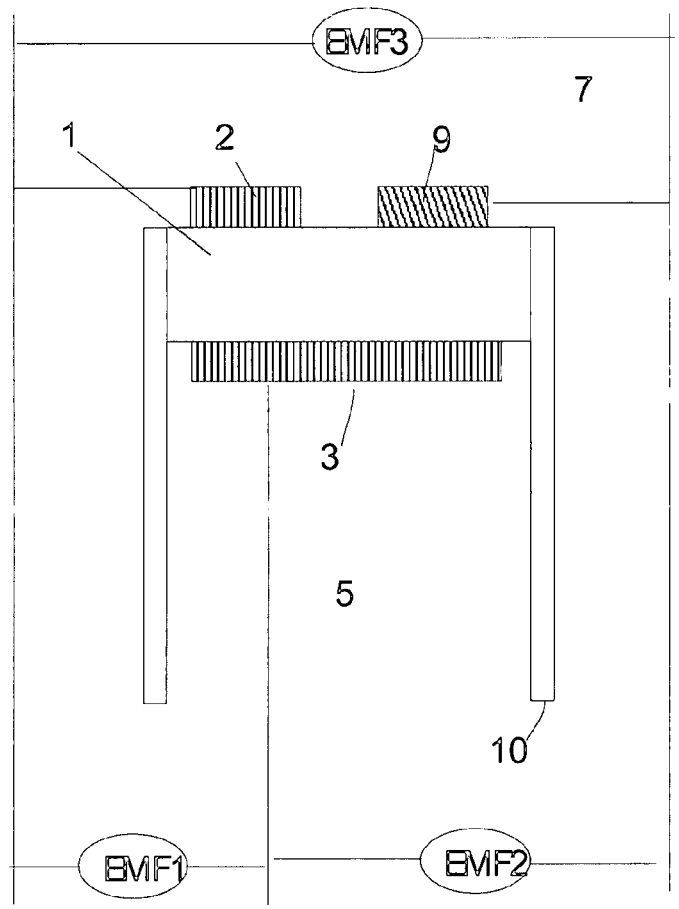
Figure 4. Schematic diagram of a mixed potential sensor with two electrodes exposed to analyzed gas and referenced electrode exposed to air reference (type 2).
1- Solid electrolyte 2.- Measuring electrode; 3 – Reference Electrode, 5 Reference Air, 7 - Analyzed gas, 9- Second Measuring electrode; 10 -Impervious enclosure.

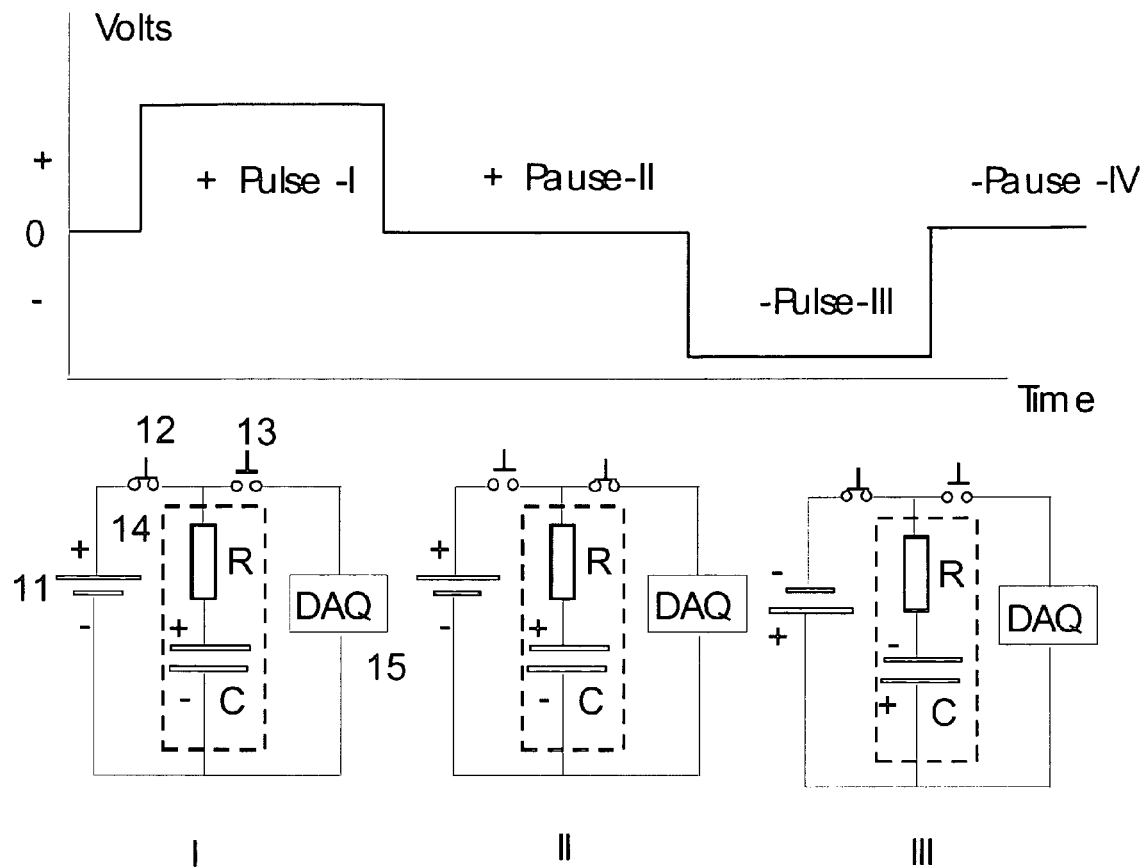
Figure 5. Schematic representation of sensor conditioning in accordance with present invention.
11-External Power supply; 12&13 automatic switches; 14 Sensor;1 5 Data Acquisition System
I. Positive Pulse; II –pause after positive pulse; III Negative pulse; IV pause after negative pulse.

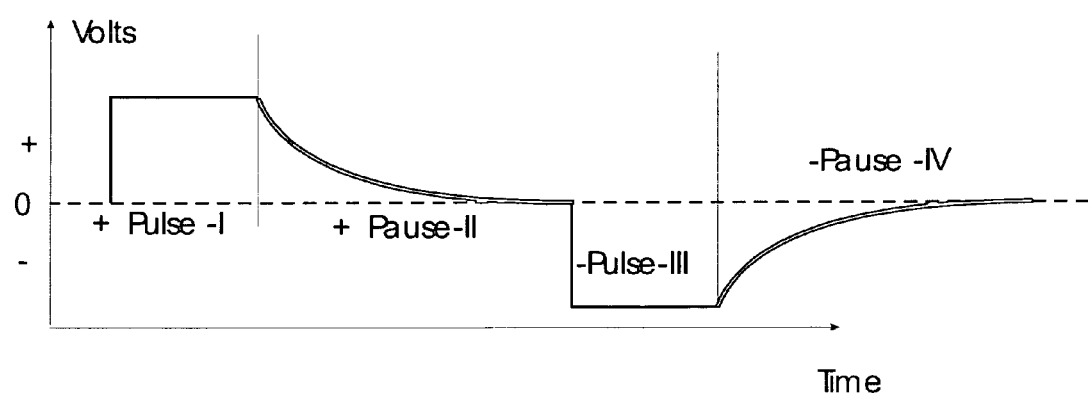
Figure 6. Sensor discharge with both electrodes exposed to air.

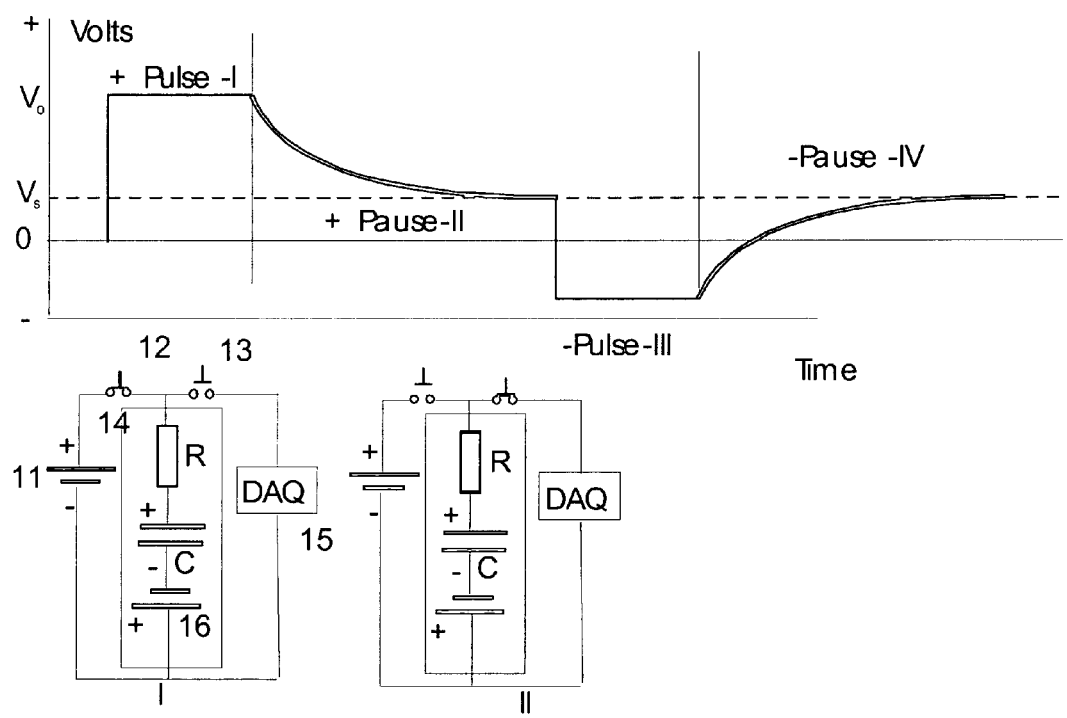
Figure 7. Sensor discharge –measurement electrode is exposed to combustion exhaust.
11. External Power supply; 12&13 automatic switches; 14 Sensor;15 Data Acquisition System, 16- Sensor output voltage in response to analyzed gas.

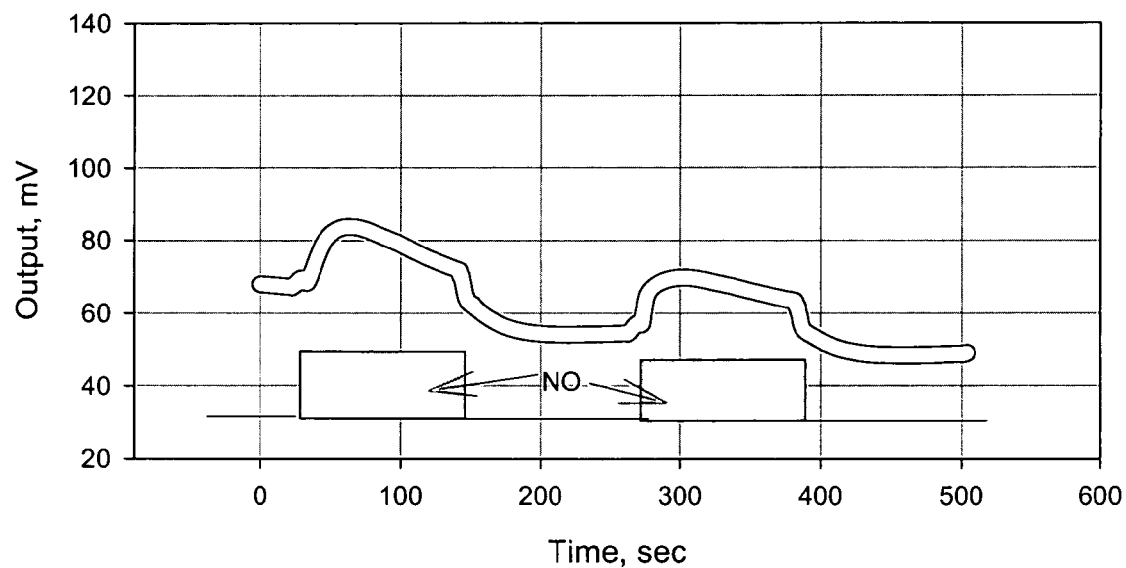
Figure 8 Response of a potentiometric Oxygen sensor to pulses of NO (0- 1000 ppm) at 3% $O_2$ without conditioning treatment.

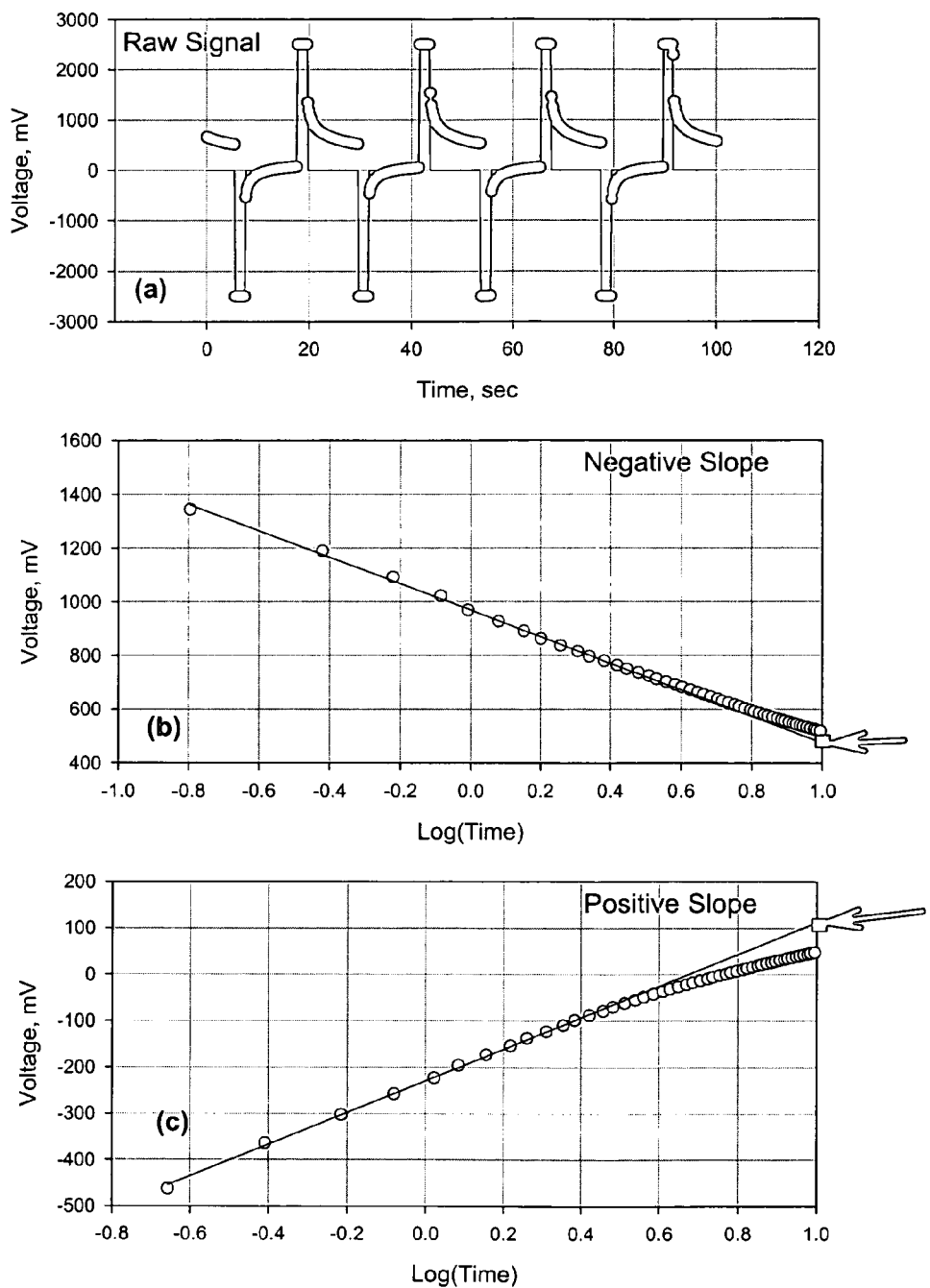

Figure 9. Raw voltage output from a potentiometric Oxygen sensor while subjected to conditioning treatment (square wave pulses with the amplitude of +/- 2.5 Volts with the duration of 2 sec separated by pauses with the duration of 10 sec) (a) (solid line represents applied voltage and filled circles represents measured sensor output) Sensor output during the pause following the positive applied voltage pulse (b) Sensor output during the pause following the negative applied voltage pulse (c)

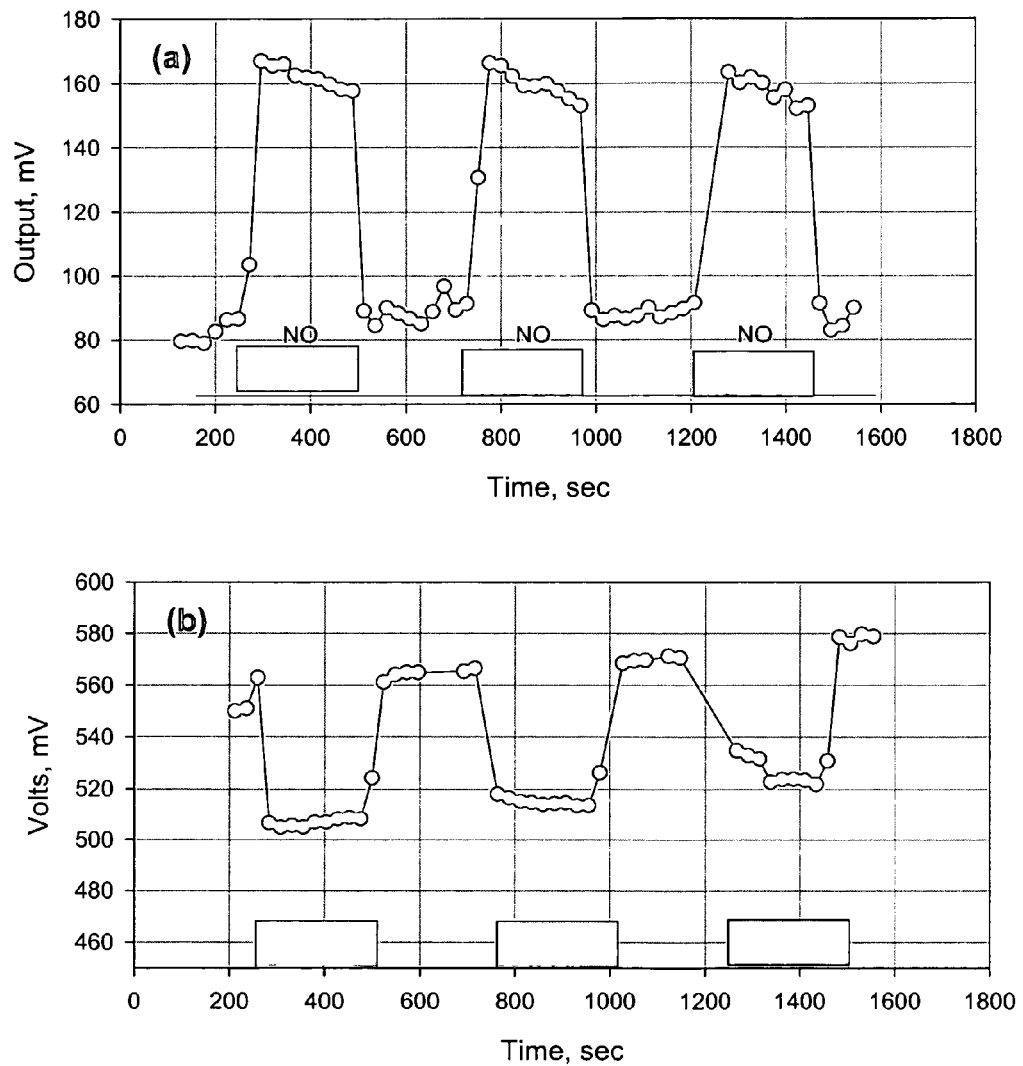
Figure 10. Response of a potentiometric Oxygen sensor to pulses of NO at concentration of 1000 ppm at 3% $O_2$ while subjected to conditioning treatment.
    (a) Response measured during the pause following the positive applied voltage pulse
    (b) Response measured during the pause following the negative applied voltage pulse

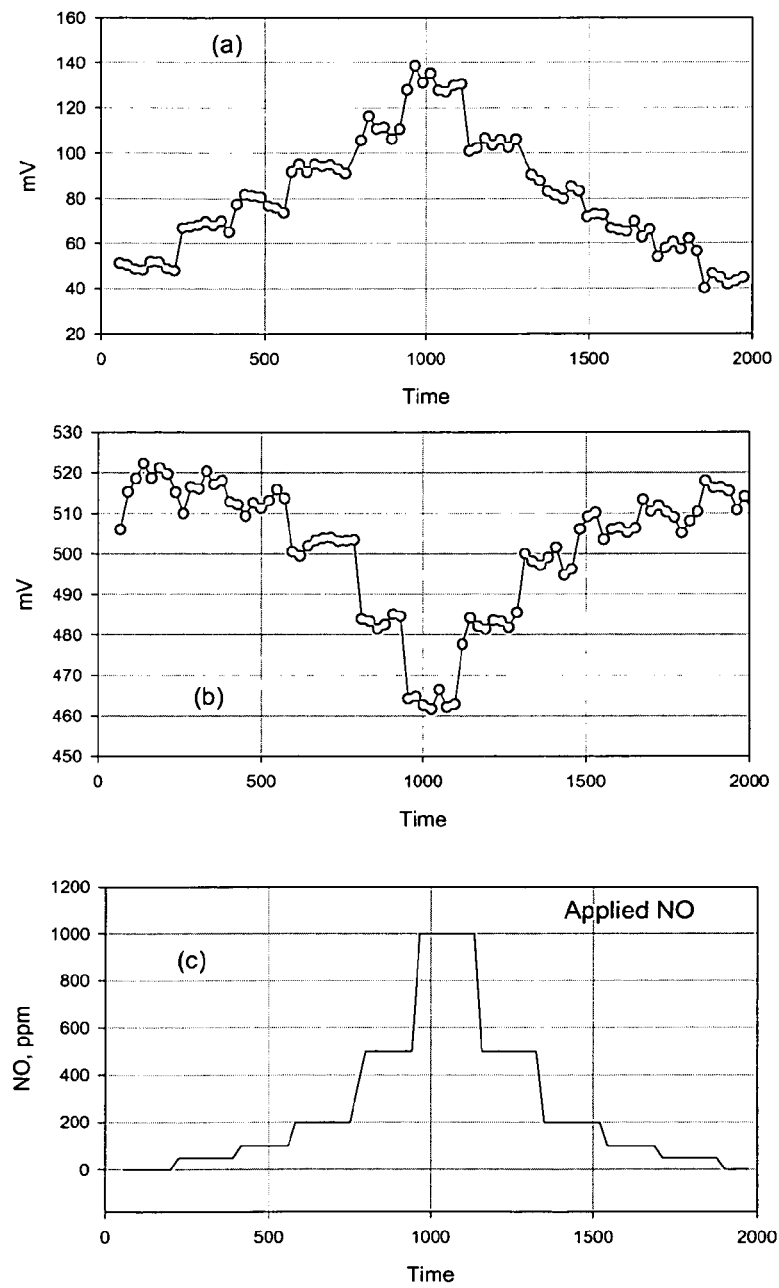
Figure 11. Response of a potentiometric Oxygen sensor to step changes of NO at 3% $O_2$ while subjected to conditioning treatment.
(a) Response measured during the pause following the positive applied voltage pulse
(b) Response measured during the pause following the negative applied voltage pulse (c) Applied NO
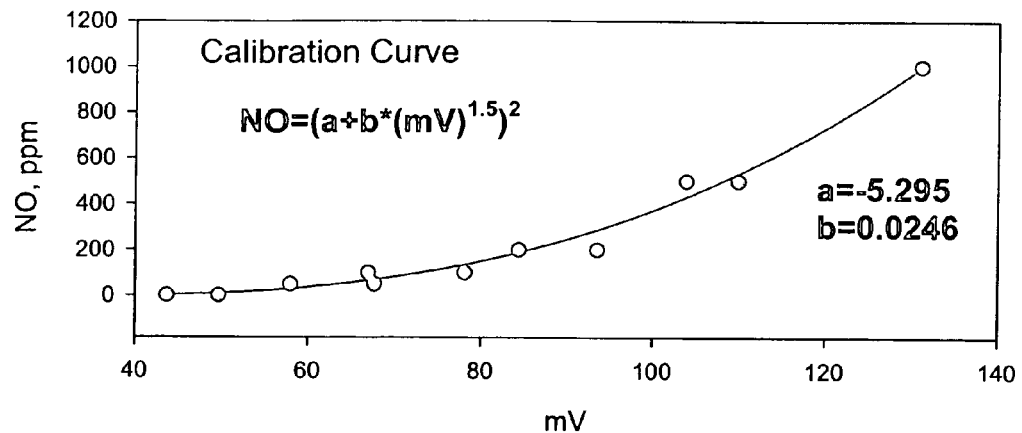
Figure 12 Calibration curve relating sensor output with the applied NO ppm concentration
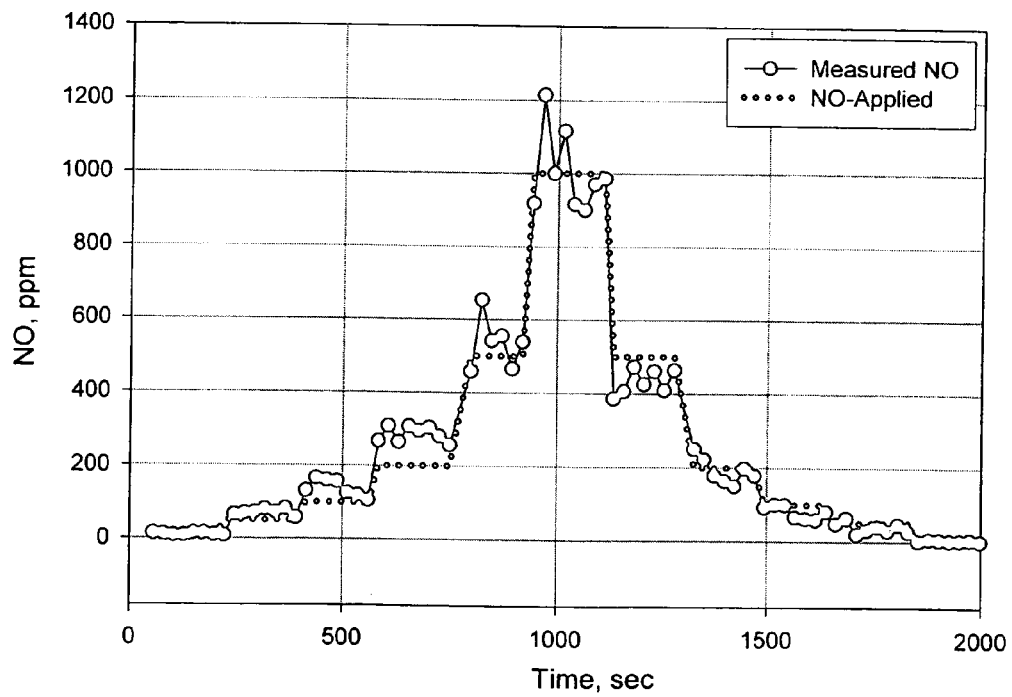
Figure 13 Measured NO ppm concentrations during step changes of NO @ 3% $O_2$.

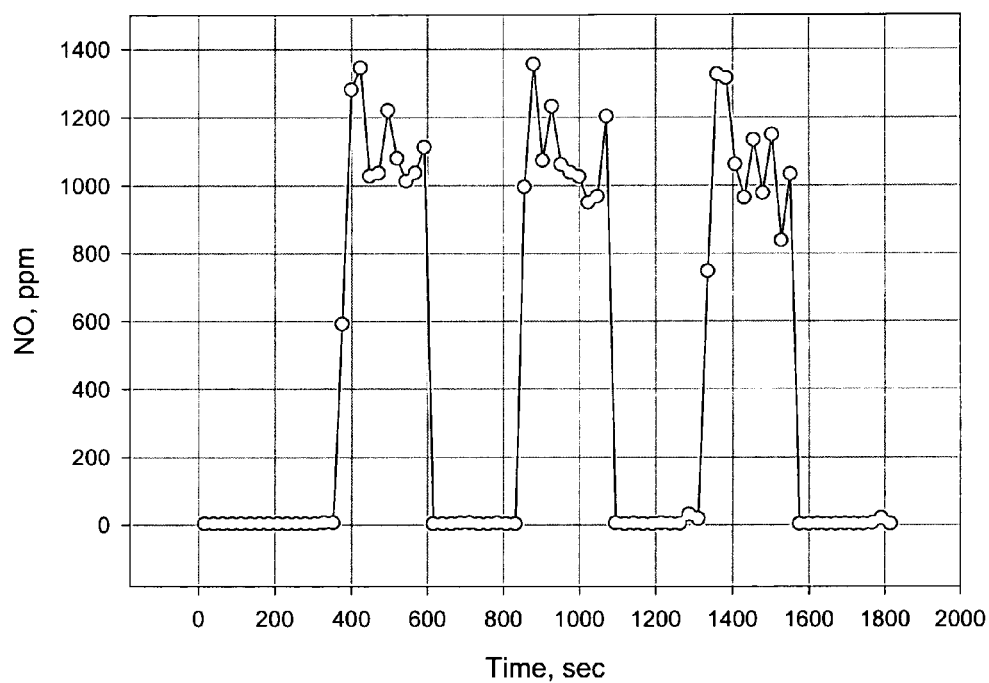
Figure 14. Measured NO ppm concentration in response to 0-1000 ppm NO pulses @ 3% $O_2$.

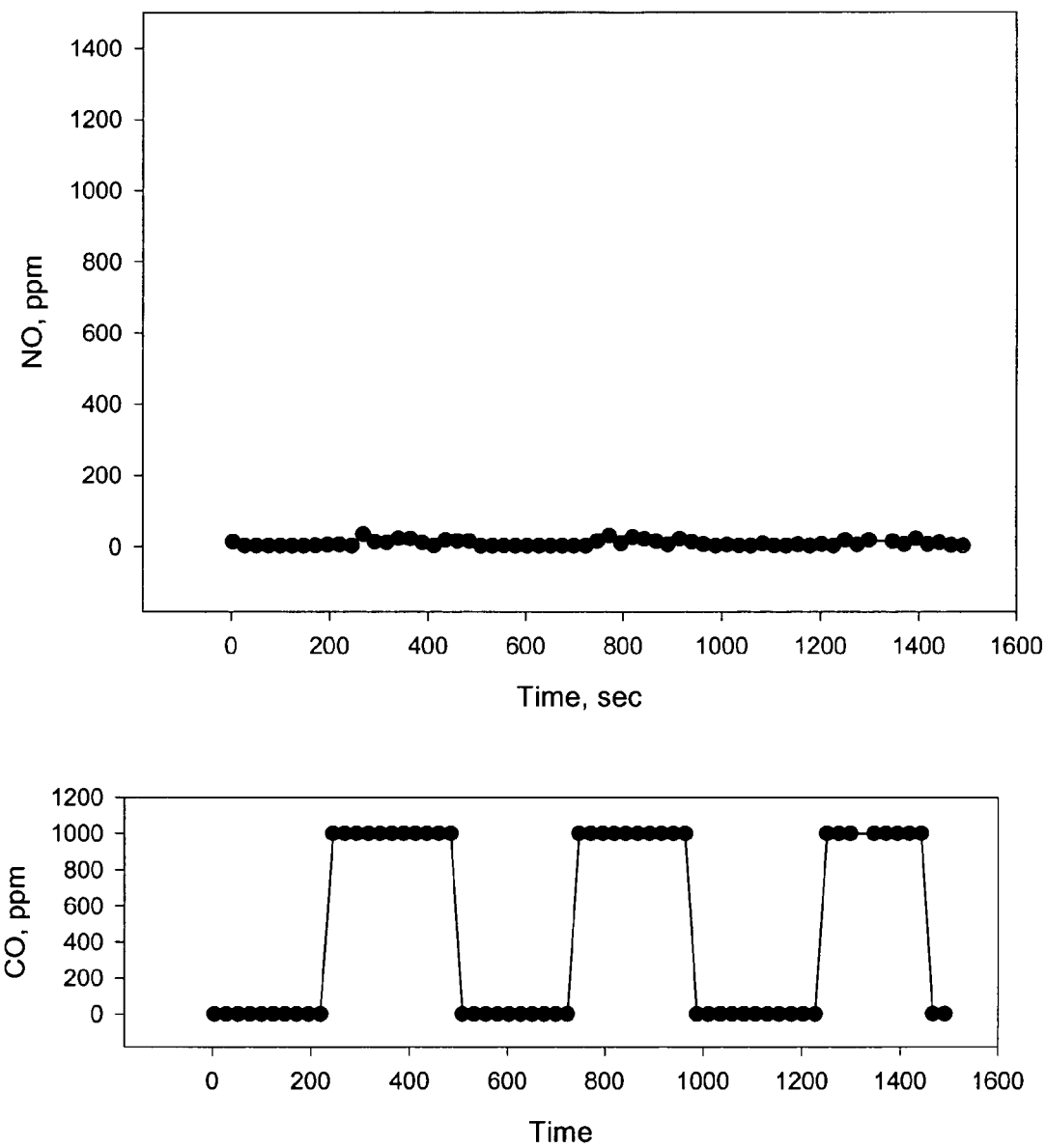
Figure 15 Interference with pulses of CO (0-1000 ppm) @ 1%O2 and NO=0ppm

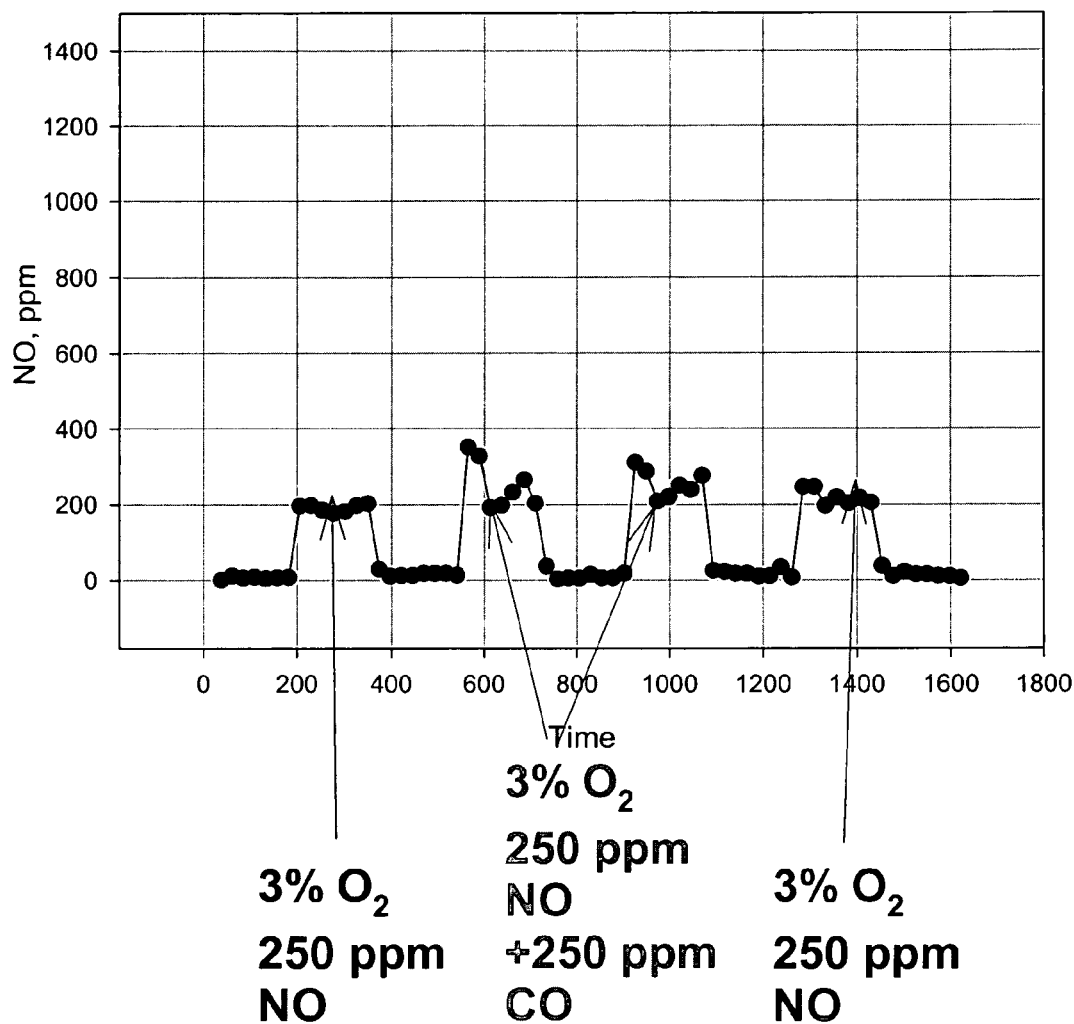
Figure 16 Interference between NO (250 ppm) and CO (250 ppm) @ 3%O2

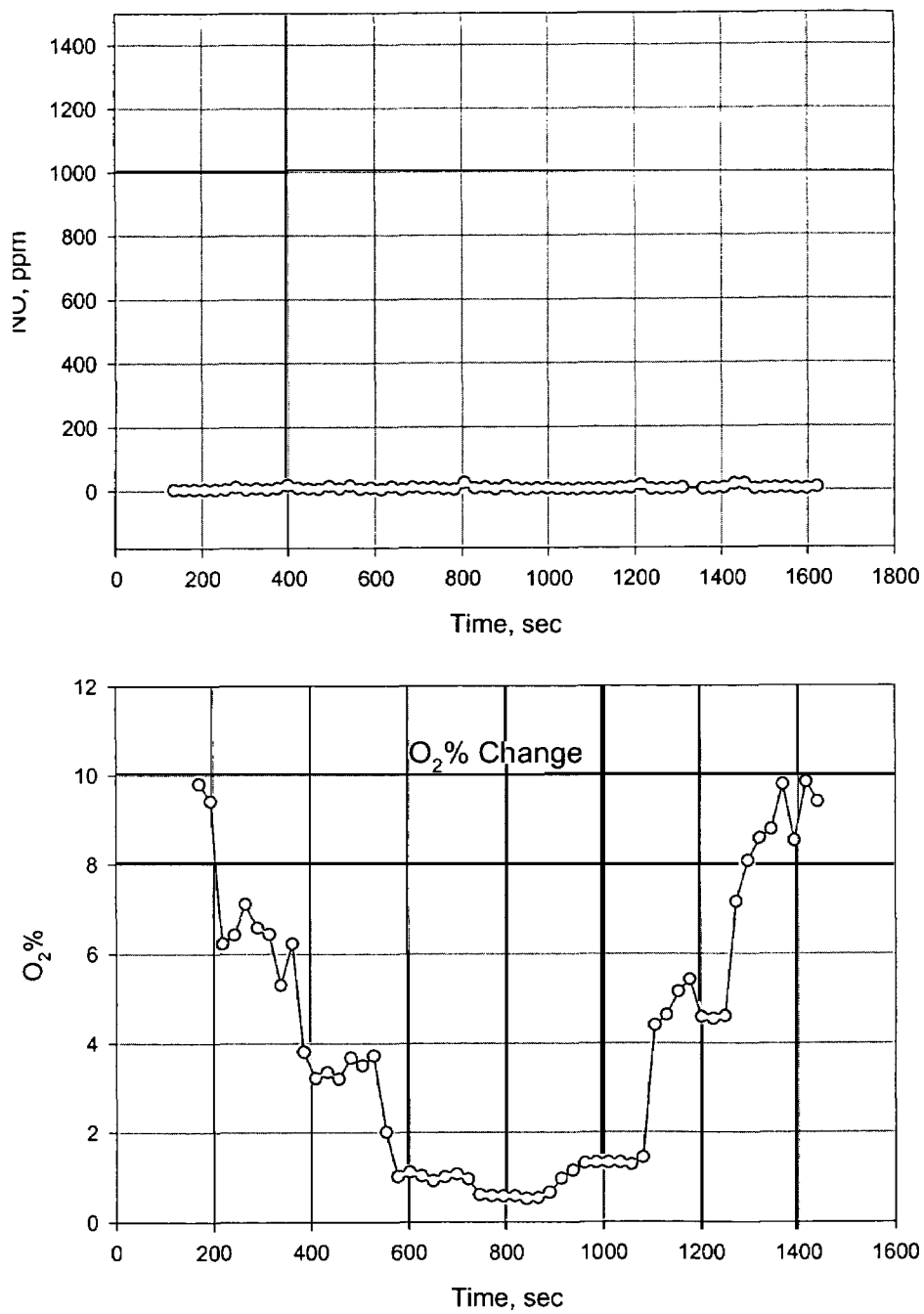
Figure 17 Interference with changes in oxygen concentration in the range 0.5-10% at NO=0 ppm.

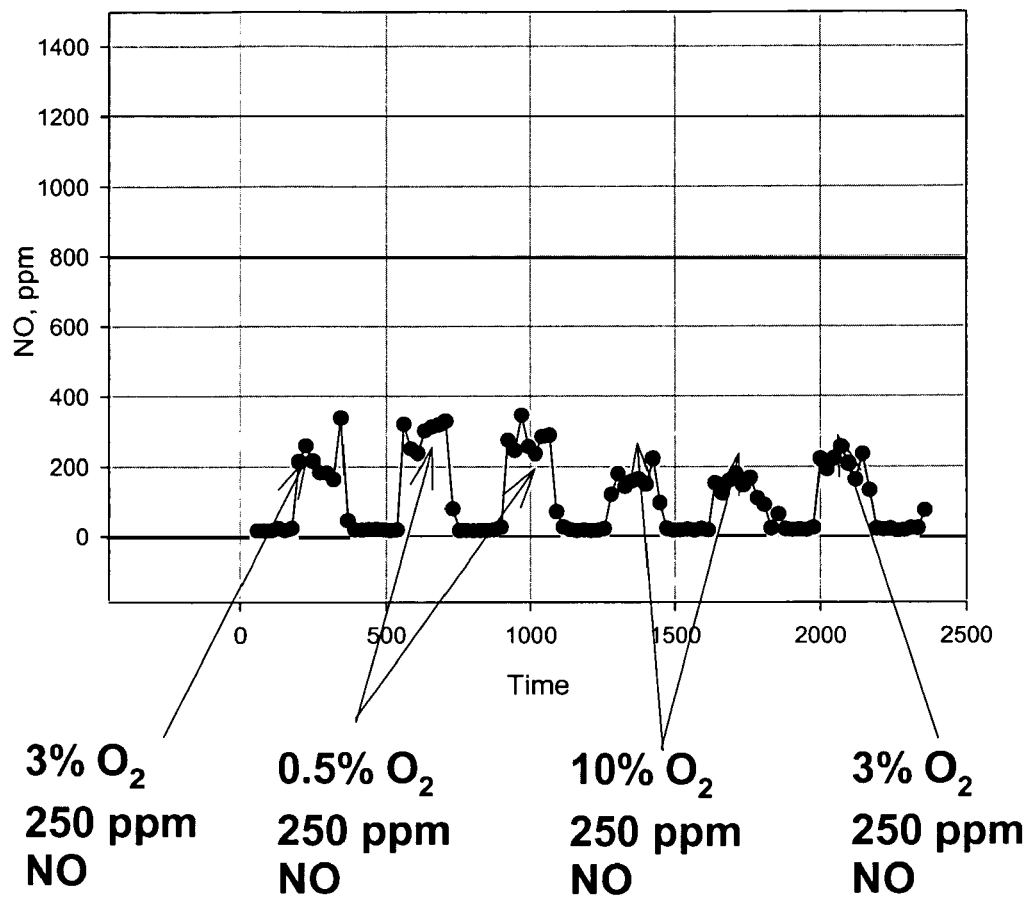
Figure 18 Interference with changes in oxygen concentration in the range 0.5-10% at NO=250 ppm.

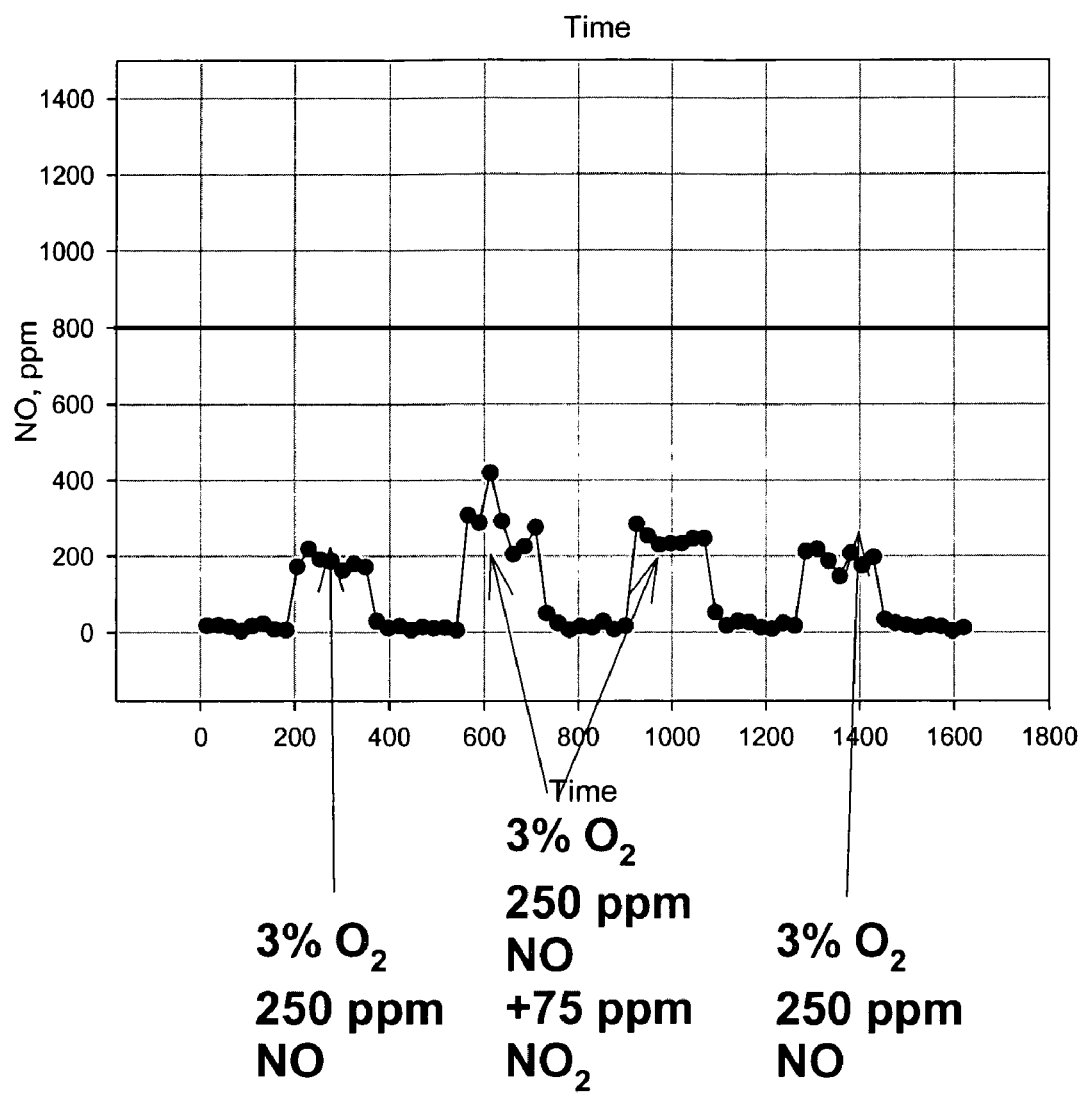
Figure 19 Interference between NO (250 ppm) and NO$_2$ (75 ppm) @ 3%O2

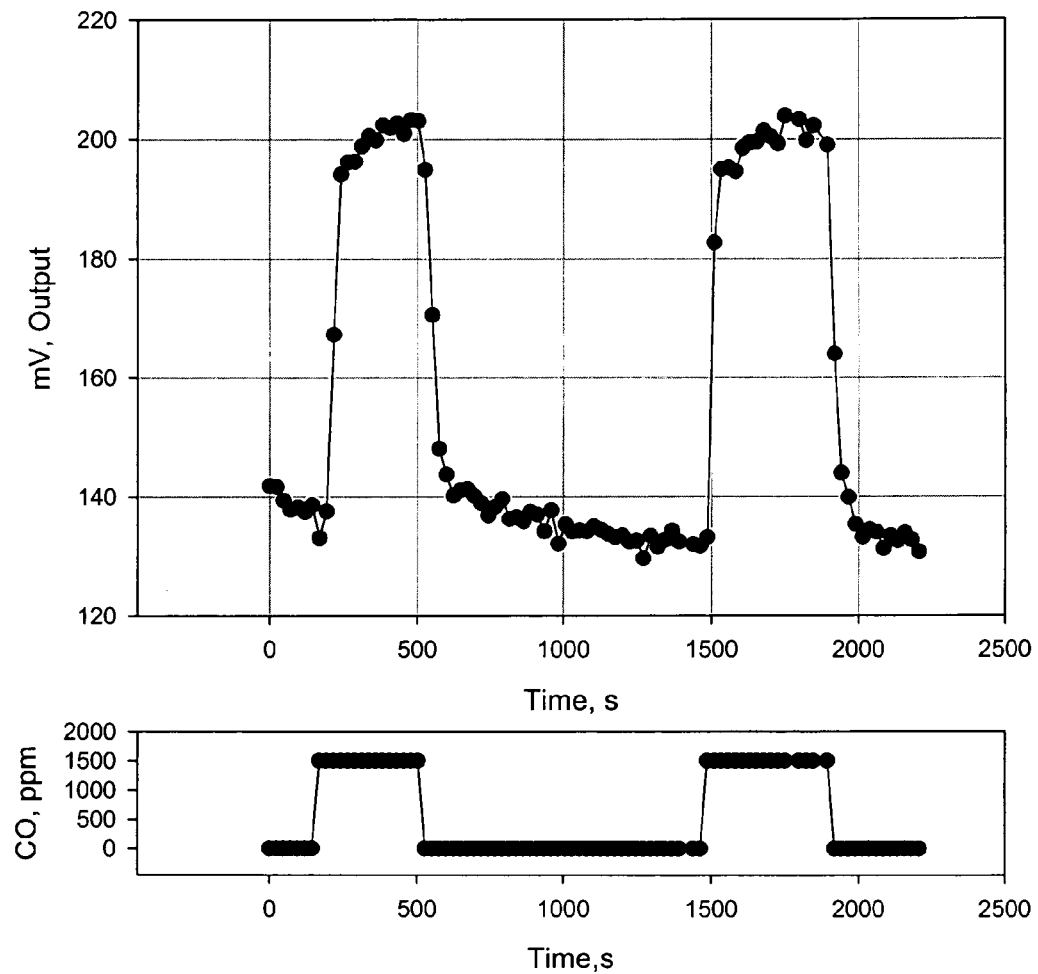
Figure 20 Response of a potentiometric Oxygen sensor to step changes of CO (0-1500 ppm) at 2% $O_2$ while subjected to conditioning treatment (square wave pulses with the amplitude of +/- 1.0 Volts).

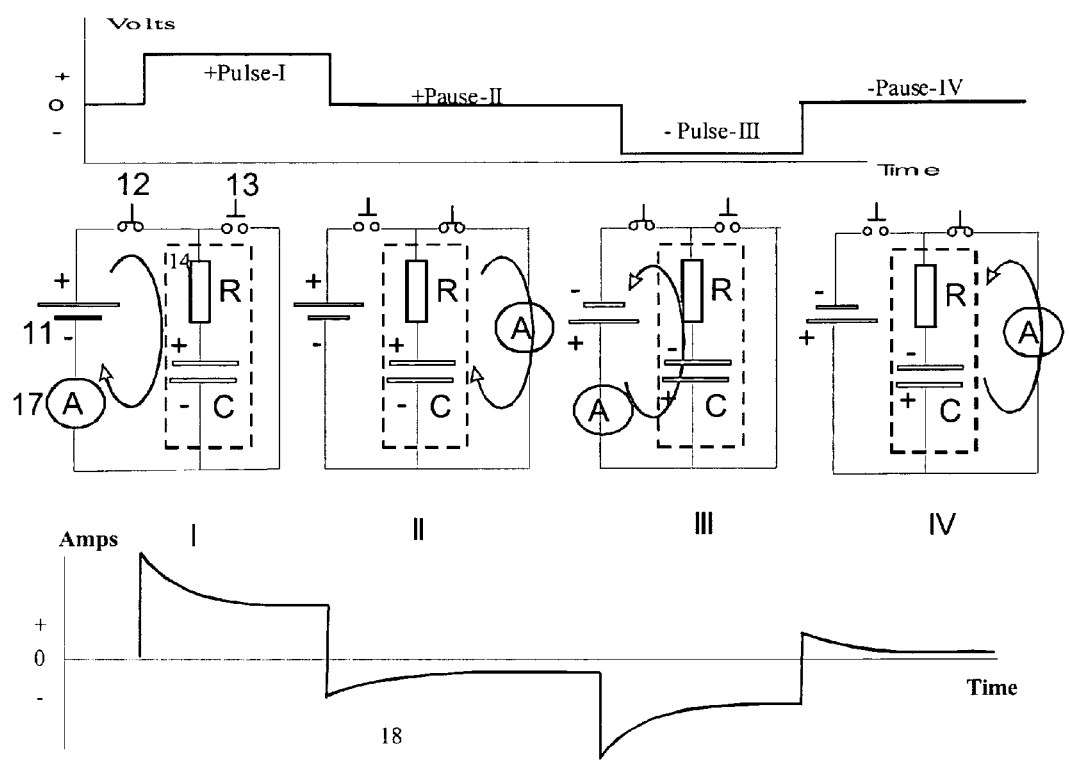
Figure 21. Sensor charging/discharging current measurements.
11. External Power supply; 12&13 automatic switches; 14 Sensor; 17 Ammeter; 18 Measured sensor current.

METHOD OF SENSOR CONDITIONING FOR IMPROVING SIGNAL OUTPUT STABILITY FOR MIXED GAS MEASUREMENTS

RELATED APPLICATIONS

The present invention claims the benefit of U.S. Provisional Patent No. 60/580,606, filed on Jun. 18, 2004 and U.S. Provisional Patent No. 60/599,513, filed on Aug. 9, 2004, both of which are incorporated by reference as if fully rewritten herein.

BACKGROUND OF THE INVENTION

1. Field of the Invention

The present invention relates generally to gas sensors and more particularly to mixed-potential gas sensors for detecting gases such as carbon monoxide, unburned hydrocarbons and nitrogen oxide, which are common in combustion exhaust.

2. Description of the Related Art

Combustion exhaust gases contain the following major components, namely $N_2$, $O_2$, CO, $CO_2$, $H_2O$, and $NO_x$. In the fuel rich region, exhaust contains excessive concentrations of CO and hydrocarbons (HC). In the fuel lean region, exhaust contains excessive concentration of NOx. Close to the stoichiometric point, exhaust contains minimal concentration of these harmful contaminants. (See FIG. 1)

To measure concentration of $O_2$ in the exhaust gas stream, a zirconia oxygen sensor is typically used. It is generally formed of a zirconia thimble having an inner and outer metal coating, usually platinum, to form an electrode (See FIG. 2). These electrodes are then used to measure the differential oxygen concentration between the measured gas on the outside of the thimble, and a reference gas, usually atmospheric air, on the inside of the thimble. By measuring the voltage between two electrodes, the differential oxygen concentration can be calculated.

Several electrochemical reactions are taking place on the electrode surface in the vicinity of triple phase boundary lines (TPBL—a line separating the Pt electrode, the analyzed gas and the Zirconia substrate):

  (1)

  (2)

  (3)

Reaction (1) takes place on both electrodes (measuring electrode-1 and reference electrode-3, see FIG. 2). Reactions 2 and 3 take place only on the measuring electrode. At elevated temperatures (>600° C.) rates of reactions (2) and (3) are negligibly small in comparison with reaction (1), which allows utilization of zirconia oxygen sensor for direct measurements of $O_2$. Sensor response in this range is described by the Nernst Equation:

$$EMF = RT/4F * Ln(P_{air}/P_{gas})$$ (4)

Where R is the perfect gas molar constant, T is absolute temperature, F is the Faraday constant, $P_{air}$ is the partial pressure of oxygen on reference side of the sensor, and $P_{gas}$ is the oxygen partial pressure on the measurement side.

At lower temperatures ($\leq 500°$ C.), rates of reactions (2) and (3) are becoming compatible with reaction (1), allowing the zirconia sensor to be used for measurements of other gases constituting combustion exhaust. Sensor response can be no longer described by the Nernst equation, typically generated sensor output is significantly higher than EMF predicted by equation (4). Since several reactions are taking place simultaneously on measurement electrode, sensor response in this range is called mixed potential.

In the range of mixed potential, oxidation reaction (2) is consuming oxygen ions in the vicinity of the active reaction sites (TPBL) and will increase the sensor output, thus the presence of an increased concentration of carbon monoxide will increase sensor output. On the other hand, reduction reaction (3) will increase the oxygen ions concentration in the vicinity of TPBL, thus the presence of increased concentrations of nitrogen monoxide will decrease the sensor output. In the range of mixed potential, a zirconia sensor has very weak response to variations of oxygen partial pressure.

Several types of mixed-potential gas sensors have been developed for combustion control and environmental monitoring processes. FIGS. 3 and 4 show examples of possible sensor configurations used for mixed potential measurements in addition to the configuration shown in FIG. 2. In FIGS. 3 and 4, both measurement electrodes are exposed to the analyzed gas. A mixed potential signal is generated due to the different catalytic activity of these measurement electrodes. These sensors clearly demonstrated strong response to the presence of carbon monoxide and nitrogen oxide; however, their lack of stability, repeatability and selectivity did not allow the development of a viable commercial sensor. (See U.S. Pat. No. 6,605,202 B1)

To improve selectivity and sensibility of the zirconia oxygen sensor, Differential Pulse Voltametry (DPV) was used (U.S. Pat. No. 5,554,269). The DPV method is comprised of superimposing biased increasing voltage applied between sensor electrodes with pulsed voltage and then measuring resulting current at the moment of abrupt voltage changes. The generated current is related to concentration of $NO_x$ present in the analyzed gas.

The drawback of DPV is related to the fact that the generated current is inversely proportional to the sensor electrode resistance. Electrode resistance usually increases due to sensor degradation, additionally, DPV involves biasing sensor electrodes with DC voltage, which will result in electrode polarization and will increase sensor resistance. Variation of electrode resistance will require frequent recalibrations to maintain reasonable accuracy.

SUMMARY OF THE INVENTION

The present invention suggests a new method for detecting concentrations of oxidizable (carbon monoxide, unburned hydrocarbons, etc) and reducible (nitrogen monoxide, etc) gases such as those present in a combustion exhaust stream. The method is based on subjecting the sensor electrodes to a conditioning treatment. Square wave (or saw tooth) voltage pulses of opposite polarity and equivalent amplitude are applied between sensor electrodes. Pulses are separated by the pauses when the charging power supply is disconnected from the sensor and the open circuit sensor discharge is recorded such as with a Data Acquisition System (DAQ). Useful information regarding the concentration of analyzed gases can be extracted by measuring the voltage decay during the pause immediately following the voltage pulse.

An alternative method involves measuring the charging current during positive or negative pulses and the discharging current during the pauses (when sensor electrodes are shunted) following voltage pulses.

The kinetics of sensor discharge is related to the net concentration of reducible/oxidizible gases, which would control the concentration of $O^{2-}$ ions in the vicinity of TPBLs according to reactions 1-3).

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 1 is a schematic representation of combustion process exhaust;

FIG. 2 is a schematic of a Zirconia Oxygen sensor;

FIG. 3 is schematic diagram of a type 1 mixed potential sensor with two electrodes exposed to analyzed gas;

FIG. 4 is a schematic diagram of a type 2 mixed potential sensor with two electrodes exposed to analyzed gas and the reference electrode exposed to air;

FIG. 5 is a schematic representation of sensor conditioning in accordance with present invention;

FIG. 6 is diagram of a discharge of the sensor with both electrodes exposed to air;

FIG. 7 is a diagram of the discharge of the sensor with measurement electrode being exposed to combustion exhaust;

FIG. 8 shows the response of a potentiometric Oxygen sensor to pulses of NO (0-1000 ppm) at 3% $O_2$ without conditioning treatment according to a known procedure;

FIG. 9 shows output from a potentiometric Oxygen sensor while subjected to conditioning treatment and explains the data processing algorithm with the proposed method according to preferred embodiment;

FIG. 10 shows response of a potentiometric Oxygen sensor to pulses of NO while subjected to conditioning treatment with proposed method according to preferred embodiment;

FIG. 11 shows response of a potentiometric Oxygen sensor to step changes of NO while subjected to conditioning treatment with the proposed method according to preferred embodiment;

FIG. 12 shows a calibration curve relating sensor output with the applied NO ppm concentration FIG. 13 shows measured NO ppm concentrations during step changes of NO with proposed method according to preferred embodiment;

FIG. 14 shows measured NO ppm concentration in response to 0-1000 ppm NO pulses with proposed method according to preferred embodiment;

FIG. 15 shows interference with pulses of CO (0-1000 ppm) and NO=0 ppm;

FIG. 16 shows interference between NO (250 ppm) and CO (250 ppm) @ 3% O2;

FIG. 17 shows interference with changes in oxygen concentration in the range 0.5-10% at NO=0 ppm;

FIG. 18 shows interference with changes in oxygen concentration in the range 0.5-10% at NO=250 ppm.

FIG. 19 shows interference between NO (250 ppm) and $NO_2$ (75 ppm) @ 3% O2;

FIG. 20 shows response of a potentiometric Oxygen sensor to step changes of CO with proposed method according to preferred embodiment; and FIG. 21 is a diagram of a sensor charging/discharging current measurements.

DESCRIPTION OF THE PREFERRED EMBODIMENTS

The best mode for carrying out the invention is presented in terms of its preferred embodiment as an be applied to different types of known oxygen sensors including but not limited to:

1. Traditional zirconia oxygen sensor (8) as shown in FIG. 2. The sensor is generally formed of a zirconia thimble (1), having an inner platinum coating (3) and an outer platinum coating (2) to form a reference and measuring electrodes. The reference electrode is usually exposed to ambient air (5) and the measuring electrode is exposed to analyzed gas (7). Electromotive Force (EMF) measured between measuring and reference electrodes is used to obtain partial oxygen pressure in the analyzed gas.

2. Mixed potential sensor (type 1) as shown in FIG. 3. Both electrodes of the sensor (2 and 9) are exposed to analyzed gas.

3. Mixed potential sensor (type 2) as shown in FIG. 4. Sensor has two measuring electrodes (2 and 9) exposed to the analyzed gas and a reference electrode (3) usually exposed to air.

4. Lambda sensors—both thimble type and planar multi-layer design.

A schematic diagram of a proposed conditioning treatment is shown in FIG. 5. Sensor (14) is represented by resistor R and capacitor C connected in series. During a positive Pulse (I) the sensor is connected with a power supply (11) by closing the switch (12) and opening switch (13). The measuring sensor electrode (exposed to analyzed gas) is charged positively according to the polarity of power supply. During the pause (II), switch 12 is open and switch 13 is closed. Sensor electrodes are disconnected from the power supply and an open circuit sensor discharge is recorded with a Data Acquisition System (DAQ). At the end of the pause, sensor electrodes are disconnected from DAQ and connected to the power supply, but with reverse polarity (III). The measuring sensor electrode is charged negatively. At the end of the negative pulse, sensor electrodes are again disconnected from the power supply and reconnected with DAQ by opening switch 12 and closing switch 13 and sensor discharge is recoded with DAQ. At the end of the pause, sensor electrodes are connected again with power supply with direct polarity, and the process will repeat itself.

In another aspect of the present invention, DAQ can be permanently connected to the analyzed sensor and only switch 12 is used to connect and disconnect sensor electrodes from the power supply.

For a traditional oxygen sensor, Voltage is applied between the reference and measuring electrodes (2 and 3, see FIG. 2). For a mixed potential sensor of type 1,—voltage is applied between two measuring electrodes (2 and 9 see FIG. 3). For a mixed potential sensor of type 2,—voltage can be applied either between two measurement electrodes (2 and 9) or between each of the measurement and reference electrode (2 and 3, or 9 and 3 see FIG. 4).

When both sensor electrodes are exposed to air, the sensor generates zero output voltage. In this case, a sensor charged negatively/or positively will completely discharge after negative/or positive pulses, provided that the pause between pulses is long enough (See FIG. 6).

If the measurement electrode is exposed to combustion exhaust, the sensor will generate a voltage output ($V_s$, see FIG. 7) (either according to Nernst equation (4), or according to mixed potential response). Superimposition of positive/or negative pulses will result in a discharge kinetic as shown in FIG. 7. Sensor output ($V_s$) can be extracted from discharge kinetics in several ways:
1) Pause duration between pulses is long enough and sensor can be completely discharged to the level of $V_s$.
2) Kinetics of sensor discharge can be described by equation of capacitor discharge.

$$V=V_s+V_o*\exp(-t/RC), \quad (5)$$

where $V_o$ is positive/negative pulse amplitude, t is time, R is the sensor resistance and C is sensor capacitance. By measuring initial discharge slope, $V_s$ values can be extrapolated, which will allow faster measurements by reducing pause durations.

EXAMPLE 1

Nitrogen Oxide (NO) Measurements

According to one example of the preferred embodiment of the present invention a concentration of NO was measured by using a traditional zirconia oxygen sensor and the proposed conditioning treatment. An Exhaust Gas Oxygen sensor (EGO)(capable of accurate measurements of oxygen concentrations in a wide range 0.5-10%) was placed inside a heated furnace with the temperature of ~510° C. The sensor was equipped with an internal heater and the heater voltage was set at V=10 Volts. The sensor measurement electrode was exposed to different mixtures of $N_2$; $O_2$; NO; $NO_2$, and CO gases, simulating conditions in the combustion process exhaust.

To demonstrate advantages of the proposed method, we first exposed sensor to pulse changes in the concentration of NO (0-1000 ppm) at $O_2$ concentration of 3% (balance $N_2$). FIG. 8 shows the EGO sensor mV response to applied NO. Sensor response is rather weak (<15 mV) and shows significant drift of the base line. This behavior is typical for traditional zirconia oxygen sensors at relatively low operating temperatures. (See "Progress in mixed—potential type devices based on solid electrolyte for sensing redox gases" by N. Miura, G. Lu, N. Yamazoe, Solid State Ionics v. 136-137, pp 533-542, 2000")

This type of sensor response cannot be directly utilized to measure NO concentration due to significant drift of the output.

FIG. 9(a) shows sensor output signal while subjected to conditioning treatment in accordance with the present invention. The conditioning treatment involved square wave pulses with the amplitude of +/−2.5 Volts and with the duration of 2 sec. Pulses were separated by pauses (with the duration of 10 sec), when the sensor electrodes were disconnected from the power supply. Solid line in FIG. 9(a) shows applied voltage and filled circles show voltages measured with DAQ. Sensor discharge during pauses following positive and negative voltage pulses was approximated by equation (5). Results of the curve fitting procedure are shown in FIGS. 9(b) and 9(c). Initial parts of the discharge curves can be approximated by a straight line in semi-logarithmic coordinates. The fitting line was extrapolated to pause duration t=10 sec. Filled squares and arrows in FIGS. 9(b) and 9(c) show the resulting extrapolated voltages. These voltages were subsequently used to measure sensor response to analyzed gases under conditioning treatment according to a preferred embodiment of the present invention.

FIG. 10 shows response of the EGO sensor to pulse changes in the concentration of NO by using the sensor conditioning treatment measured in the same test set up as shown in FIG. 8. The conditioning treatment resulted in significant amplification of the sensor response to the analyzed gas (NO) from 15 to ~80 mV and significantly reduced drift of the sensor base line signal (at NO=0 ppm). The achieved improvements are the most pronounced for sensor response measured during the pause following positive voltage pulses. Activation of the sensor measurement electrodes with positive Voltage pulses resulted in an increase of the sensor output in response to applied NO, while activation of the sensor measurement electrodes with negative Voltage pulses resulted in a decrease of the sensor output in response to applied NO (see FIGS. 10(a) and 10(b)).

FIG. 11 shows sensor response to step changes of NO (0;50;100;200;500;1000;500;200;100;50;0 ppm) while subjected to the conditioning treatment. Sensor response is strong and shows little hysteresis.

Data shown in FIG. 11(a) were used to establish a calibration curve relating the concentration of NO with the sensor response, which is shown in FIG. 12. This calibration curve was used to directly measure NO concentration in the analyzed gas under conditions of step changes in NO concentrations (0;50;100;200;500;1000;500;200;100;50;0 ppm) (see FIG. 13) or during pulse changes in NO (0-1000 ppm) (see FIG. 14). In both cases, the sensor conditioning treatment resulted in stable and repeatable sensor output in response to the analyzed gas.

As seen in FIG. 1 combustion exhaust contain mixed gases $O_2$, NO, CO etc. Cross-interference of sensor output is an important factor in providing reliable measurements of the individual gases in the mixture. We verified interference of the EGO sensor response to CO and $O_2$ variations while subjecting sensor to conditioning treatment. Desirable range of NO detection for a combustion process is 0-1000 ppm. Provided data will show interference with other gases at low (NO=0 ppm) and mid range (NO=250 ppm) NO concentrations. FIG. 15 shows that sensor response to 1000 ppm CO (at NO=0 ppm) is not exceeding 30 ppm NO. Interference of 250 ppm CO at 250 ppm NO is 49+/−45 ppm NO (See FIG. 16)

Interference of $O_2$ in the range of 0.5-10% is not exceeding 25 ppm NO (at NO=0 ppm) (See FIG. 17) and it is 61+/−25 ppm NO (at NO=250 ppm) (see FIG. 18)

FIG. 19 shows effect of the addition of 75 ppm $NO_2$ to 250 ppm NO in the gas mix. The resulting shift in the sensor output is 78+/−30 ppm, providing direct evidence that the preferred embodiment of the present invention allow measurements of combined concentrations of NO+$NO_2$ ($NO_x$).

EXAMPLE 2

Measurements of CO

Sensitivity to different gases in the exhaust gas mixture can be varied in the preferred embodiment of the present invention by varying amplitude of the conditioning voltage pulses. FIG. 20 shows sensor response to 1500 ppm CO (at 2% $O_2$) while subjecting the sensor to conditioning treatment with the amplitude of conditioning voltage pulses=1 Volts. Sensor sensitivity to CO has significantly improved as compared with the conditioning treatment with the voltage amplitude of 2.5 Volts An alternative method of CO/NOx detection can be based on measuring the charge/discharge current during pulses and pauses. FIG. 21 shows a diagram of these measurements. Sensor (14) is represented by resistor R and capacitor C connected in series. During a positive Pulse (I), the sensor is connected with the power supply (11) by closing the switch

(12) and opening switch (13). The measuring sensor electrode (exposed to analyzed gas) is charged positively according to the polarity of power supply. The kinetics of sensor charging is recorded with an ammeter (17). During the pause (II), switch 12 is open and switch 13 is closed. Sensor electrodes are disconnected from the power supply and shunted via the ammeter. The sensor discharge current is recorded with the ammeter (17). At the end of the pause, the shunt between sensor electrodes is removed and the electrodes are connected with the power supply, but with reverse polarity (III). The measuring sensor electrode is charged negatively, and the kinetics of sensor charging is recorded with the ammeter (17). At the end of the negative pulse, sensor electrodes are again disconnected from the power supply and shunted via the ammeter by opening switch 12 and closing switch 13. Sensor discharge current is recorded with the ammeter (17). At the end of the pause, sensor electrodes are connected again to the power supply with direct polarity, and the process will repeat itself. The kinetics of charge/discharge current will reflect oxidation-reduction reaction rates and will be related to the concentration of CO and NOx in the ambient gas.

Advantages of our proposed method of sensor conditioning as demonstrated in examples 1 and 2 can be summarized as following 1. Positive and negative pulses have equivalent amplitude and are not causing net polarization of sensor electrodes.
2. It is improving sensor stability by refreshing active reaction sites via fresh supply of $O^{2-}$ ions in each cycle preventing an accumulation of charge from redox reactions. It can also potentially prevent the poisonous effects of minute constituents of the exhaust stream ($SO_2/SO_3$ for example), which normally interfere and mask the response to analyzed CO/NO gases.
3. Applied voltage amplitude and pulse duration can be selected to improve sensitivity to a particular analyzed gas (CO or $NO_x$). Reactions 2 and 3 described above can be accelerated by applying positive or negative potential.
4. Proposed sensor conditioning can be applied to traditional zirconia $O_2$ sensor with one electrode exposed to analyzed gas and reference electrode exposed to air. It can be also applied to sensors with two electrodes exposed to the analyzed gas, which generate mixed potential response due to different catalytic activity of two electrodes.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. An improved method of measuring a gas or combined gas concentration utilizing an oxygen sensor, said method comprises the steps:
    a. applying a sequence of square wave pulses to electrodes on a sensor for first, fixed durations, each of said pulses alternate between a positive and a negative pulse;
    b. measuring charge current during each of said positive and negative pulses;
    c. disconnecting said electrodes from a power supply between the positive and negative pulses for a pause period of a second, fixed duration; and,
    d. approximating sensor discharges during each of said pulses.

2. The method of claim 1, wherein said first fixed duration is 2 seconds.

3. The method of claim 1, wherein said pause period is 10 seconds.

4. The method of claim 1, wherein pulses are applied with an amplitude of +/−2.5 Volts for said first fixed duration of 2 seconds.

5. The method of claim 1, wherein said pulses are applied with a varied amplitude, said varied amplitude is ± 1 Volt for said, fixed duration of 2 seconds.

6. The method of claim 1, wherein said sensor discharge is approximated by equation $$V = V_s + V_o \cdot \exp\left(\frac{-t}{R \cdot C}\right),$$

wherein $V_o$ is pulse amplitude, t is said duration, R is sensor resistance, C is sensor capacitance, and $V_s$ is initial discharge slope.

* * * * *